United States Patent [19]

Burton et al.

[11] Patent Number: 4,471,142
[45] Date of Patent: Sep. 11, 1984

[54] PROCESS FOR PRODUCING ISOPROPYL ALCOHOL AND DI-ISOPROPYL ETHER

[75] Inventors: Paul E. Burton, Garwood; William E. Wellman, Edison, both of N.J.

[73] Assignee: Exxon Research & Engineering Co., Florham Park, N.J.

[21] Appl. No.: 379,883

[22] Filed: May 19, 1982

[51] Int. Cl.$^3$ .................... C07C 27/00; C07C 29/06; C07C 41/00; C07C 43/04
[52] U.S. Cl. .................................. 568/696; 568/889
[58] Field of Search ............................... 568/696, 889

[56] References Cited

FOREIGN PATENT DOCUMENTS 522620 3/1956 Canada ............................... 568/889
843671 8/1960 United Kingdom ................. 568/696

Primary Examiner—J. E. Evans
Attorney, Agent, or Firm—Jack B. Murray, Jr.

[57] ABSTRACT

An improved process for indirect hydration of propylene to form di-isopropyl ether and isopropyl alcohol is provided in which propylene is absorbed in sulfuric acid to form an extract which is withdrawn from the absorbing zone; water in carefully controlled amounts is admixed with the extract and the resulting mixture is passed to an ether generating zone to form a vaporous ether product and a bottoms product depleted in di-isopropyl ether and containing sulfuric acid in a concentration at least equal to the acid concentration in the extract withdrawn from the absorbing zone. The withdrawn bottoms is then divided into two portions: a first portion is recycled to the absorber; and the second such portion is admixed with sufficient water to hydrate absorbed olefin values and the resulting mixture is fed to an alcohol generator for formation of isopropyl alcohol as overhead product and dilute sulfuric acid as bottoms product.

7 Claims, 1 Drawing Figure

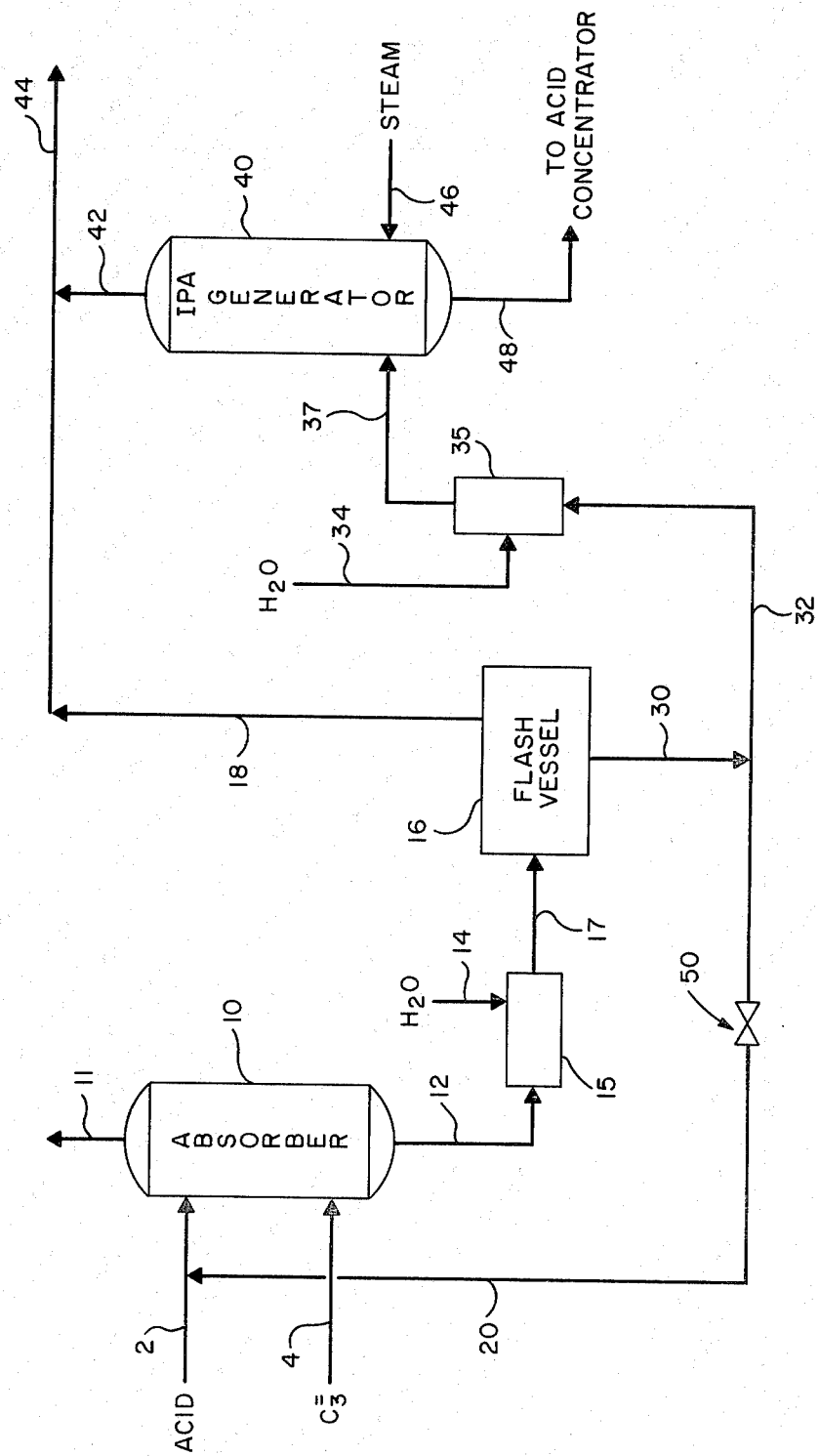

4,471,142

PROCESS FOR PRODUCING ISOPROPYL ALCOHOL AND DI-ISOPROPYL ETHER

BACKGROUND OF THE INVENTION

1. Field of the Invention

This invention relates to the manufacture of diisopropyl ether and isopropyl alcohol, and more specifically to the indirect hydration of propylene for formation of di-isopropyl ether and isopropyl alcohol.

2. Description of the Prior Art

Large volumes of alcohols and ethers are produced annually by the catalytic hydration of olefins, in which the selected olefin feed is absorbed in a concentrated sulfuric acid stream to form an "extract" containing the corresponding alkyl ester of the sulfuric acid. Thereafter, water is admixed with the ester-containing extract to hydrolyze the ester and to form the desired alcohol and ether which are then recovered, generally by stripping with steam or some other heating fluid in an alcohol generator. There is thereby produced a diluted sulfuric acid stream which is then generally treated to concentrate it with respect to sulfuric acid for recycle to the absorption stage.

In these conventional processes, the amount of by-product di-isopropyl ether can be increased slightly by varying the reaction condition, e.g., by increasing the ratio of reacted propylene to sulfuric acid, but a major change in di-isopropyl ether production cannot be easily realized.

U.S. Pat. No. 2,105,508 relates to a process for producing di-isopropyl ether (DIPE) by absorption of propylene. The extract liquid is passed from the absorption tower and introduced, after the addition of water or steam (to compensate for the water reacting to form the ether) to one of a series of ether generating pots, each equipped with steam coils. A vaporous product containing DIPE and the corresponding alcohol, isopropyl alcohol (IPA), is withdrawn, treated in a soda scrubber and passed to a distillation tower. Unreacted propylene is recovered as overheads in the distillation tower and can be recycled to the absorber. A sidestream of condensed ether vapors is withdrawn from the top of the distillation tower, and an IPA-containing liquor is formed as bottoms product. The alcoholic bottoms is then, with or without removal of water, refluxed to the ether generating pots or passed to further refining as alcohol. Spent acid liquor remaining in the ether generating pots is recycled to the absorber.

Reflux of the alcoholic bottoms to the ether generating pots is said to permit more accurate control of the ether generating conditions therein and to permit the acid to be concentrated to a higher strength before recycle to the absorber.

British Pat. No. 535,111 relates to a process for manufacture of ethers from olefins in which the sulfuric acid extract liquid is removed from the absorbing tower and is partially stripped in a stripping tower to form an ether-alcohol overhead mixture and a partially stripped extract as bottoms. The overhead mixture is passed to a separate tower for separation of the ether and to form an alcohol-containing bottoms. These alcohol-containing bottoms from the last tower are combined with the partially stripped extract, and sufficient water is added to make up that used in the formation of the ether. The resulting liquid stream is then recycled as the absorbate to the top of the absorbing tower.

In U.S. Pat. No. 2,216,931, aliphatic ethers such as di-isopropyl ether are produced by a process in which the sulfuric acid extract containing olefin values is split into two portions: a first portion is passed, after addition of water, to a stripping tower for formation of a vaporous overhead comprising the corresponding alcohol; and a second portion is fed directly to a reaction tower, together with the vaporous alcohol overhead formed in the stripping tower. In the reaction tower a liquid overhead stream is withdrawn and then passed to a generator for formation of vapors, which are then fed into a fractionating tower for recovery of the di-isopropyl ether product as overhead and to form a bottoms product comprising isopropyl alcohol. This alcohol bottoms is then admixed with the stream containing the alcohol vapors withdrawn from the stripping tower for feed to the reaction tower. A dilute sulfuric acid stream is withdrawn as bottoms from the generator and is then concentrated for eventual recycle to the absorbing stage.

In U.S. Pat. No. 2,533,808, the extract liquid is diluted with water and then passed to an alcohol generator for formation of dilute sulfuric acid as bottoms and to form overhead vapors comprising isopropyl alcohol and di-isopropyl ether. This vapor product is then treated to separate the isopropyl alcohol as product and to recover the di-isopropyl ether, which is recycled to the absorbing stage. In this process, the production of isopropyl alcohol can be increased by the recycle of the di-isopropyl ether.

In the process of U.S. Pat. No. 2,609,400, the propylene sulfuric acid extract liquid is stripped without dilution with water in a generator-stripper to form a mixture of ether and alcohol vapors. The partially stripped acid extract is then admixed with sufficient water (which can be added as steam via the steam injection into the stripper) to replace the water consumed in forming the alcohol and ether thus removed. Careful regulation of the extract temperature, steam temperature and pressure, and use of hot stripping gas is required to so control the heat balance of the generator-stripper to avoid dilution of the acid. Partially stripped acid extract is withdrawn from the generator-stripper and recycled to the olefin absorber, together with make-up acid as required. The ether/alcohol vapors withdrawn from the generator-stripper are scrubbed with a caustic solution to remove entrained acid, and the acid-free vapors are then condensed. The condensate, which comprises predominantly isopropyl alcohol, can be distilled to separate DIPE, which can be at least in part admixed with the partially stripped acid extract for recycle to the absorber.

In U.S. Pat. No. 2,994,721, the extract is passed into an ether generation zone from which vapors comprising predominantly di-isopropyl ether are withdrawn as overhead. The remaining liquids are then diluted with water and fed to an alcohol generator for formation of overhead vapors comprising isopropyl alcohol and some di-isopropyl ether. Again, a dilute acid is withdrawn as bottoms product from the alcohol generator for concentration and subsequent recycle to the absorbing stage.

In German Offenlegungsschrift No. 2,759,237 propylene is absorbed in sulfuric acid to form an extract which is then treated to liberate the ether and alcohol. After separation of the alcohol, the ether is recycled to make more alcohol.

None of the foregoing processes are readily adaptable to produce widely varying ratios of co-product isopropyl alcohol and di-isopropyl ether.

SUMMARY OF THE INVENTION

According to the improved process of the present invention, propylene is contacted in an absorbing zone with aqueous sulfuric acid for formation of a liquid extract comprising sulfuric acid containing absorbed propylene values. The extract is contacted with a carefully controlled amount of water and the resulting hydrated extract is passed to an ether generating zone in which the hydrated extract is treated to liberate vapors containing diisopropyl ether and to form a liquid bottoms product comprising a depleted sulfuric acid extract containing absorbed propylene values and having a sulfuric acid concentration at least equal to the acid concentration in the extract liquid. The depleted extract is divided into two streams: the first stream is passed to an alcohol generator, after addition of water, to form an overhead product comprising predominantly isopropyl alcohol and a bottoms product comprising a dilute sulfuric acid stream; and the second portion of said bottoms product is recycled to the absorbing zone.

BRIEF DESCRIPTION OF THE DRAWING

FIG. 1 is a diagrammatic illustration of one embodiment of the process of this invention.

DETAILED DESCRIPTION OF THE INVENTION

According to the improved process of this invention, di-isopropyl ether and isopropyl alcohol are produced in amounts which can be carefully controlled to increase or decrease the production of by-product di-isopropyl ether, as desired, without the need to employ expensive catalysts.

In the process, propylene is passed to an absorbing zone wherein it is contacted with a concentrated sulfuric acid stream to form an extract containing sulfuric acid and absorbed propylene values.

The propylene may be obtained from any available source, such as the destructive distillation of carbonaceous materials, but particularly from the cracking of petroleum hydrocarbons such as is practiced in the petroleum refining of mineral oils. The propylene may be conventionally obtained by careful fractionation of cracked petroleum gases and is preferably free of higher unsaturates, particularly diolefins, such as butadiene, etc.

The sulfuric acid which is passed through the absorbing zone should have a sulfuric acid strength of between 50 and 80 wt. %, preferably between 55 and 70 wt. %, and more preferably between 60 and 70 wt. %.

The absorbing zone will generally employ a temperature of between about 50° and 120° C., more preferably from about 85° to 115° C. The absorption of the propylene in the sulfuric acid, according to this invention, is carried out under increased pressures, which should be sufficient to keep the absorbed propylene in the liquid phase, but may otherwise vary within wide limits. Pressures of from 50 to 500 psig, preferably from 150 to 300 psig, have been found favorable for a rapid and extensive absorption of the propylene in the sulfuric acid and its conversion thereby into isopropyl ester.

Good contact between the propylene, or the mixture containing it, and the absorbing acid is important. This may be achieved, for instance, by efficient agitation or by the use of absorption towers, preferably in countercurrent flow. The absorption may be continued, if desired, until the concentration of propylene in the gaseous effluent from the absorbing zone has been reduced to below about 5% by weight, and it will therefore be understood that propylene of any concentration higher than 5% in the feed can be treated.

The extent of absorption in a countercurrent system such as a series of agitator vessels and intermediates separators will depend not only on the relative amount of acid employed, but also on the length (number of stages) and capacity of the system and on the rate of throughput. Mixtures of relatively low propylene content will require a greater number of stages under otherwise similar conditions to obtain a given degree of extraction. A molar proportion of 1.6 to 1, propylene to acid, with a liquid mixture containing 40% propylene will give satisfactory absorption within an economical time, while with about 90% propylene or more it will become possible to increase the molar proportion to 1.9, and even 2.0, to 1 without impairing the efficiency of the absorption.

The extract which is withdrawn as liquid product from the absorbing zone contains water, sulfuric acid, generally in a concentration of from about 35 to 65 wt. %, and preferably from about 45 to 55 wt. %, and absorbed propylene values. As used herein, the term "absorbed propylene values" is intended to refer to all molecules in the liquid which contain propyl ($C_3H_7$) or propylene ($C_3H_6$) moieties, such as propyl esters of sulfuric acid, free isopropyl alcohol and free di-isopropyl ether. (Weight % propylene values are calculated and reported herein on the basis of $C_3H_6$ moieties.) Free isopropyl alcohol is generally present in the extract in an amount of from about 10 to 45 wt. %. The extract can also contain free di-isopropyl ether, which if present will be generally in a concentration of less than about 15 wt. %, preferably from about 3 to 6 wt. %.

Thereafter, in a first water mixing zone, which can comprise a separate vessel or one or more portions of the conduit containing the extract itself, water is added in an amount sufficient to provide the moles of water stoichiometrically required to form the amount of di-isopropyl ether and isopropyl alcohol to be withdrawn as vapor from the subsequent ether generation zone. Thus, water will be generally added to the extract in the first water mixing zone in an amount of from about 0.01 to 2.0, and preferably from about 0.5 to 1.0, moles of water for each mole of di-isopropyl ether and isopropyl alcohol withdrawn as vapor in the ether generation zone. While the precise amount of di-isopropyl ether vapors so formed will vary widely depending on the concentration of absorbed propylene in the extract, the temperature and pressure in both the first water addition zone and the ether generation zone, and a variety of other factors, water will be generally added to the extract in an amount of from about 0.5 to 6.0 wt. %, more preferably from about 1.0 to 2.0 wt. %, based on weight of the extract. The conditions under which this controlled amount of water is added can also vary widely. Generally the temperature of the extract will range from about 85° to 110° C. The conditions of pressure under which the water is added are also not critical, and pressures within the range of from about 10 to 300 psig are entirely satisfactory.

The water admixed with the extract should be substantially completely reacted to avoid the undesired dilution of the extract to an acid strength unsuitable for recycle to the absorber after separation of the di-isopropyl ether vapor. It is desirable to provide sufficient residence time for the reaction mixture to reach equilibrium in order to maximize the yield of di-isopropyl ether. To this end, a liquid residence time of from about 0.5 to 4.0 hours, preferably from about 1.0 to 2.0 hours, should be provided in the first water mixing zone.

Following the addition of water to the extract, the liquid so formed (herein termed the "hydrated extract"), is introduced to the ether generation zone wherein the hydrated extract is treated under conditions sufficient to form vapors comprising di-isopropyl ether and isopropyl alcohol, which can be recovered therefrom. These vapors will generally comprise from about 30 to 50 wt. % of di-isopropyl ether, with the balance comprising isopropyl alcohol, propylene and free water.

The ether generation zone comprises conventional equipment such as one or more single stage flash zones with integral heaters, conventional regenerators (packed or with bubble cap, etc.) and kettles with integral heaters. A stripping gas such as nitrogen, but preferably propylene, may be used to aid in the recovery of the ether. The ether generating zone may be heated by conventional means such as by heating surfaces in contact with the hydrated extract, heating pumparound streams, heating inlet streams and stripping gas, if used, and similar methods.

The liquid withdrawn from the flashing zone, herein termed the "depleted extract", generally comprises from about 5 to 35 wt. % absorbed propylene values, and from about 40 to 65 wt. % sulfuric acid and the balance water. According to the improved process of this invention, at least a portion of this depleted extract is recycled to the absorbing zone. The sulfuric acid concentration in this recycle liquid is preferably at least equal to and more preferably is from about 1.05 to 1.2 times greater than the acid concentration of the liquid extract withdrawn from the absorber. The portion of the depleted extract which is thus recycled can vary widely but will generally comprise at least about 30 wt. %, preferably from about 30 to 65 wt. %, more preferably from about 40 to 55 wt. % of the depleted extract withdrawn from the ether generating zone.

The portion of the depleted extract which is not so recycled, is contacted with an additional quantity of water in a second water addition zone (which can also comprise a separate vessel or a conduit containing the liquid to be contacted) to dilute the sulfuric acid to a strength of from about 35 to 65 wt. %, preferably from about 45 to 60 wt. %. The liquid residence time provided in this second water addition zone can vary widely, with times of from 0.01 to 1.0 hours being typical. The diluted liquid is then passed to a distillation zone, herein termed the "alcohol generator", for generation of an overhead product comprising isopropyl alcohol and di-isopropyl ether together with any remaining propylene and some water. The overhead product, which will generally comprise at least about 50 wt. % of isopropyl alcohol, can then be combined with the vapors withdrawn from the ether generation zone, described above, and processed using conventional methods to recover and purify the desired di-isopropyl ether and isopropyl alcohol products, and for recycle to the process, if desired, of any recovered propylene.

The conditions or temperature and pressure which are employed in the alcohol generator are not critical to this invention. Thus, bottoms temperatures of from about 75° to 200° C., preferably from about 100° to 180° C., are suitable and the pressure in the alcohol generator can comprise atmospheric, subatmospheric or superatmospheric pressure (e.g., from 0.1 to 10 atmospheres). Temperatures or pressures outside of this range can be employed if desired.

The liquid bottoms which are withdrawn from the alcohol generator comprise spent sulfuric acid and generally contain from about 45 to 65 wt. % sulfuric acid. This dilute sulfuric acid can be concentrated if desired employing conventional technology, which does not form part of this invention, for ultimate recycle to the absorbing stage to absorb additional quantities of propylene.

The improved process of this invention can be further exemplified by reference to the accompanying drawing, wherein one embodiment of the process is illustrated. In the illustrated continuous process, an aqueous, concentrated sulfuric acid stream, containing from about 60 to 70 wt. % sulfuric acid, is introduced into absorber 10 via conduit 2 for countercurrent contact with gaseous propylene which is introduced into absorber 10 via conduit 4. Absorber 10, is operated at a temperature within a range of from 85° to 115° C. and a pressure from about 150 to 300 psig provides efficient countercurrent contracting, as by means of countercurrent absorbing tower. An extract liquid is formed therein comprising from about 40 to 65 wt. % sulfuric acid, from about 10 to 40 wt. % absorbed propylene values and the balance water, and is withdrawn from the lower portion of absorber 10 via conduit 12. Unabsorbed gases, comprising propylene, are withdrawn from the upper portion of absorber 10 via conduit 11, and can be recovered and recycled if desired or scrubbed and passed to waste.

The extract liquid in line 12 is passed to mixing zone 15 wherein it is contacted with water, introduced thereto via conduit 14, in an amount of up to about 10 wt. % water, and preferably from about 1.5 to 6 wt. % water, based on the weight of absorbed propylene values in the extract liquid.

Mixing zone 15 can comprise any suitable conventional liquid/liquid contacting vessel, or can comprise a portion of the conduits 12 or 17. In the latter case, the water is introduced via conduit 14 directly into conduits 12 or 17 and a suitable length of conduit should then be provided between the water-introduction point and flash vessel 16 to permit the desired complete mixing and reaction of the water with the propyl-sulfuric acid ester for ether generation.

The resulting mixture is passed via conduit 17 to flash zone 16 which is operated, for example, at a temperature within the range of from 80° to 100° C. and a pressure from about 5 to 10 psig. From flash zone 16 there is withdrawn an overhead vapor comprising, for example, from about 30 to 50 wt. % di-isopropyl ether and from about 30 to 40 wt. % isopropyl alcohol, together with from about 10 to 20 wt. % propylene, via conduit 18. Liquid which is withdrawn from flash zone 16 via conduit 30 comprises the depleted extract and contains, for example, from about 5 to 35 wt. % absorbed propylene values, from about 45 to 65 wt. % sulfuric acid, and the balance water.

The depleted extract is divided into two portions. A first portion, generally comprising from about 30 to 70 wt. % (and preferably from about 40 to 60 wt. %) of the total depleted extract, is passed as recycle to the upper portion of absorber 10 via conduits 20 and 2. The remaining portion of the depleted extract, generally comprising from about 70 to 30 wt. % (and preferably from about 60 to 40 wt. %) of the depleted extract, is passed via conduit 32 to second water mixing zone 35 wherein it is contacted with water which is introduced thereto via conduit 34, in an amount of from about 35 to 100 parts by weight of water per part by weight of the absorbed propylene values in the depleted extract. As in zone 15, second water mixing zone 35 can comprise a separate vessel or a portion of conduits 32 or 37. The liquid residence time in zone 35 generally ranges from about 0.1 to 2 hours, preferably from about 1 to 30 minutes. The resulting aqueous mixture is passed to conduit 37 to alcohol generator 40 wherein the mixture is heated, as by means of direct injection of steam via conduit 46, for formation of alcohol vapors as an overhead product, which is withdrawn via conduit 42. Generator 40 is generally operated at a bottoms temperature of from about 70°–130° C., and preferably 80°–120° C., and at a bottoms pressure of from about 1 to 50 psig, more preferably 5 to 20 psig. The vapors in conduit 42 comprise isopropyl alcohol, di-isopropyl ether, and minor amounts of propylene and water, and, if desired, can be combined with the vapors in conduit 18 and passed to conduit 44 for conventional product separation and finishing steps (not shown).

A spent sulfuric acid stream, comprising from about 45 to 55 wt. % sulfuric acid is withdrawn via conduit 48 from the lower portion of generator 40 and can be passed to conventional acid-concentration steps (not shown) for ultimate recycle to conduit 2 and thence to absorber 10.

The relative proportions of di-isopropyl ether and isopropyl alcohol which are produced by the process of this invention can be varied widely, and these products will generally be produced in a di-isopropyl ether:isopropyl alcohol volume:volume ratio of from about 1:20 to 5:1 or more, and more generally from about 1:9 to 1:3, based on the total quantity of the ether and alcohol produced in conduit 44. This production ratio can be ascertained by determining the concentration and flow rates of total di-isopropyl ether and isopropyl alcohol in conduit 44 such as by use of a conventional on-line gas chromatographic analyzer (not shown) in combination with conventional flow metering devices (also not shown).

Control of this di-isopropyl ether:isopropyl alcohol production ratio can be effected by control of the relative amount of liquid flows in conduits 32 and 20. The flow rate of liquid recycle in conduit 20 can be controlled by suitable means, such as for example by provision of valve 50 in conduit 20. Most preferably, control valve 50 is operated to increase or decrease the liquid split ratio, R, which is defined by the following equation:

$$R = F_{20}/F_{32} \qquad (1)$$

wherein $F_{20}$ is the mass flow rate of liquid through conduit 20 and $F_{32}$ is the mass flow rate of liquid through conduit 32. Thus, to increase the di-isopropyl ether: isopropyl alcohol production ratio, and therefore to produce more di-isopropyl ether relative to isopropyl alcohol, the ratio "R" can be increased by adjusting valve 50 to allow the appropriate additional quantity of liquid in conduit 30 to pass into conduit 20.

As the quantity of liquid flowing through conduit 20 is increased, it is necessary to also increase the quantity of water introduced via conduit 14 accordingly, to introduce the water necessary to provide the water of reaction required to form the isopropyl alcohol and di-isopropyl ether in flash vessel 16.

As has been explained above, the sulfuric acid concentration in recycle stream 20 will generally be from about 0.5 to 1.3 times, preferably from about 1.05 to 1.2 times greater than, the acid concentration of the liquid extract 12 withdrawn from absorber 10. Therefore, the amount of water introduced via conduit 14 is preferably not greater than the amount of free water in conduit 18 plus the water of reaction required to form the isopropyl alcohol and di-isopropyl ether withdrawn from vessel 14 via conduit 18.

Correspondingly, the di-isopropyl ether:isopropyl alcohol product ratio can be decreased by increasing the isopropyl alcohol production rate relative to that of the ether product. This can be accomplished by decreasing the liquid split ratio "R" by suitably adjusting the position of valve 50 to decrease the amount of liquid recycled via conduit 20 and hence increase the amount of liquid which is passed from conduit 30 into conduit 32 for ultimate feed to isopropyl alcohol generator 40. As before, the amount of water introduced via conduit 14 will then be reduced accordingly, in view of the decreased amount of products to be formed in flash vessel 16.

The adjustment of liquid split ratio "R" alone does not substantially alter the total product production rate, that is the total moles per unit time of di-isopropyl ether and isopropyl alcohol. Rather, adjustment of this liquid split ratio alone increases (or decreases) di-isopropyl ether at the expense of isopropyl alcohol production. The total product production rate can be increased (or decreased) by increasing (or decreasing) the amount of the olefin and acid fed to absorber 10 via conduits 4 and 2, respectively, employing conventional techniques (as by use of suitable valve means, not shown).

The precise amount by which valve 50 must be adjusted to effect a given change in liquid split ratio, R, and the precise amount by which the di-isopropyl ether:isopropyl alcohol production ratio and/or the total ether and alcohol production rate will change for each step change of either the liquid split ratio "R" or the absorbate and olefin feedrates, will vary widely depending on such factors as the sulfuric acid concentration of the absorbate, the efficiency of absorber 10 in absorbing the olefin, the conditions employed in flash vessel 16 and generator 40, and other factors, and can be readily ascertained by one having ordinary skill in the art by routine experimentation.

It will be obvious that various changes and modifications may be made without departing from the invention and it is intended, therefore, that all matter contained in the foregoing description shall be interpreted as illustrative only and not limitative of the invention.

What is claimed is:

1. An improved process for the indirect hydration of propylene to form di-isopropyl ether and isopropyl alcohol which comprises:
   (a) contacting gaseous propylene with sulfuric acid in an absorbing zone to form an extract liquid containing sulfuric acid and absorbed propylene values;
   (b) contacting said extract liquid with water in a first water mixing zone to form a hydrated extract;
   (c) subjecting said hydrated extract to conditions sufficient to form a vaporous ether product containing di-isopropyl ether and a depleted extract bottoms product, depleted in absorbed propylene values and containing sulfuric acid in a concentration at least equal to the acid concentration in said extract liquid passed as feed to said first water mixing zone;

(d) recycling from about 30 to 65 weight percent of said depleted extract to said absorbing zone and contacting the remaining portion of said depleted extract with water in a second water mixing zone; and (e) subjecting the aqueous mixture withdrawn from said second water mixing zone to distillation to obtain a vaporous overhead product comprising isopropyl alcohol and a spent sulfuric acid as bottoms product.

2. The process according to claim 1 wherein water is added in said first water mixing zone in an amount of up to about 10 wt. %, based on the weight of the total extract liquid thus contacted.

3. The process according to claim 2 wherein a liquid residence time of from about 0.5 to 4 hours is provided in said first water mixing zone.

4. The process according to claim 1 wherein said depleted extract contains sulfuric acid in a concentration of from about 0.5 to 1.3 times the sulfuric acid concentration in said extract liquid passed as feed to said first water mixing zone.

5. The process according to claim 1 wherein the sulfuric acid fed to said absorbing zone is fed as an acid stream containing from about 50 to 80 wt. % sulfuric acid, said extract liquid contains sulfuric acid in a concentration of from about 35 to 65 wt. % and said depleted extract contains sulfuric acid in the concentration of from about 40 to 65 wt. %.

6. The process according to claim 1 wherein said depleted extract has a sulfuric acid concentration of from about 40 to 70 wt. % and wherein water is introduced in said second water mixing zone in an amount sufficient to provide an aqueous mixture containing from 35 to 65 wt. % sulfuric acid which is passed as feed to said distillation in step (e).

7. An improved process for the indirect hydration of propylene to form di-isopropyl ether and isopropyl alcohol which comprises:

(a) contacting gaseous propylene with sulfuric acid in an absorbing zone to form an extract liquid containing sulfuric acid and absorbed propylene values;

(b) contacting said extract liquid with water in a first water mixing zone to form a hydrated extract;

(c) subjecting said hydrated extract to conditions sufficient to form a vaporous ether product containing di-isopropyl ether and a depleted extract bottoms product, depleted in absorbed propylene values and containing sulfuric acid in a concentration of from about 1.05 to 1.2 times greater than the acid concentration in said extract liquid passed as feed to said first water mixing zone;

(d) recycling from about 30 to about 65 weight percent of said depleted extract to said absorbing zone and contacting the remaining portion of said depleted extract in a second water mixing zone; and (e) subjecting the aqueous mixture withdrawn from said second water mixing zone to distillation to obtain a vaporous overhead product comprising isopropyl alcohol and a spent sulfuric acid as bottoms product.

* * * * *